United States Patent [19]
Wardle et al.

[11] Patent Number: 6,147,209
[45] Date of Patent: Nov. 14, 2000

[54] METHOD FOR MAKING NEW POLYCYCLIC POLYAMIDES AS PRECURSORS FOR ENERGETIC POLYCYCLIC POLYNITRAMINE OXIDIZERS

[75] Inventors: Robert B. Wardle, Logan; Jerald C. Hinshaw, Ogden, both of Utah

[73] Assignee: Cordant Technologies Inc., Salt Lake City, Utah

[21] Appl. No.: 07/989,369

[22] Filed: Dec. 8, 1992

Related U.S. Application Data

[62] Division of application No. 07/292,028, Dec. 21, 1988.

[51] Int. Cl.[7] .................... C06B 25/34; C07D 243/00; C07D 487/08
[52] U.S. Cl. .................... 540/556; 149/92; 149/109.6; 540/554; 564/107
[58] Field of Search ............... 149/92, 109.6; 568/924; 540/554, 556; 546/1; 564/107

[56] References Cited

U.S. PATENT DOCUMENTS

| | | | |
|---|---|---|---|
| 2,485,855 | 10/1949 | Blomquist et al. | 149/92 X |
| 4,432,902 | 2/1984 | McGuire et al. | 540/475 |
| 5,124,493 | 6/1992 | Lukasavage et al. | 568/924 |
| 5,739,325 | 4/1998 | Wardle et al. | 540/554 |

OTHER PUBLICATIONS (Classified Document (Confidential)) Polynitropolyaza Caged Explosive Part 6, A.T. Nielsen et al. Aug. 1987, Naval Weapons Ctr., China Lake, CA.

(Classified Document (Confidential)) Synthesis of a Caged Nitramine A.T. Nielsen Naval Weapons Ctr., China Lake, CA 93555–6001.

Polynitropolyaza Caged Explosives, Part 5, Mar. 1986, Naval Weapons Center, China Lake, CA.

Synthesis of 2,4,6,8,10,12–Hexabenzyl–2,4,6,8,10,12–Hexaazaisowurtzita, Arnold T. Nielsen, Chemistry Division, Research Dept., Naval Weapons Ctr., China Lake, CA.

Robert A. W. Johnstone and Anna H. Wiley, *Chem. Rev.* (1985) 85 129–170.

*Primary Examiner*—Richard D. Lovering
*Attorney, Agent, or Firm*—Pillsbury Madison & Sutro LLP

[57] ABSTRACT

Hexabenzylhexaazaisowurtzitane is converted to tetracetyl, dibenzyl azaisowurtzitane. The benzyl groups are removed by catalytic transfer hydrogenolysis leaving a pair of available nitrogens. The available nitrogens are acetylated, and the resulting intermediate is converted to CL-20 with a strong nitrating agent.

19 Claims, No Drawings

METHOD FOR MAKING NEW POLYCYCLIC POLYAMIDES AS PRECURSORS FOR ENERGETIC POLYCYCLIC POLYNITRAMINE OXIDIZERS

This is a division of application Ser. No. 07/292,028, filed Dec. 21, 1988.

The present invention is directed to caged nitrogen compounds, particularly derivatives of hexaazaisowurtzitane and to methods of synthesis of the compounds.

BACKGROUND OF THE INVENTION

Arnold T. Nielsen in a paper entitled "Synthesis of 2,4,6,8,10,12-Hexabenzyl-2,4,5,6,10,12-hexaazaisowurtzitane" describes the synthesis of the compound named in the title. This compound is hereinafter referred to as HBIW. The more formal chemical name for this compound is 2,4,6,8,10,12-hexabenzyl-2,4,6,8,10,12-hexaazatetracyclo-[5.5.0.0.$^{3,11}$0.$^{5,9}$]dodecane. Nielsen et al. in documents entitles "Polynitropolyaza Caged Explosives Parts 5 & 6" (Part 6 is classified) and "synthesis of a caged nitramine" (classified) prepared for the Naval Weapons Center, China Lake, Calif., describe the synthesis of 2,4,6,8,10,12-hexanitro-2,4,6,8,10,12-hexaayatetracyclo[5.5.0.0.$^{3,11}$0.$^{5,9}$]dodecane which is known in the propellent/explosives field as CL-20 (This compound is hereinafter referred to as CL-20). The above-identified works of Nielsen and Nielsen et al. are incorporated herein by reference.

CL-20 is an oxidizer with great potential for use in high-energy compositions, such as propellants, gassifiers, explosives or the like. CL-20 has high detonation velocity attributable to its high heat of formation. It is also advantageous because of its high density, which is a result of the cage structure. It has particular usefulness for minimum smoke formulations (generally non-aluminized formulations). It also has particular usefulness in explosive compositions.

HBIW has the following chemical structure; the indicated numbering of the carbon and nitrogen ring members are understood to apply throughout the specification.

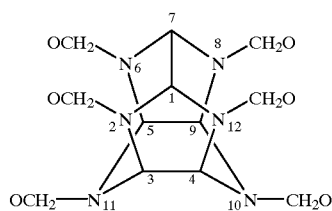

(I)

It is to be noted in the above formula that the identical 2, 6, 8, and 12 cage nitrogens are members of 5 and 6 member rings, whereas the 4 and 10 cage nitrogens are members of 6 and 7 member rings. It is found that in many chemical reactions, the four identical nitrogens react differently than the two identical nitrogens. These different nitrogens will be referred to hereinafter as the 2-6-8-12 nitrogens or the 4-10 nitrogens, respectively.

CL-20 has the following chemical structure:

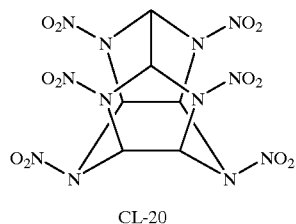

CL-20

(II)

In the first step of the procedure of converting HBIW (I) to CL-20 (II), HBIW is converted to 2,6,8,12-tetraacetyl-4,10-dibenzylhexaazaisowurtzitane, hereinafter referred to as compound IIIA, (also referred to herein as TADB) having the formula shown below:

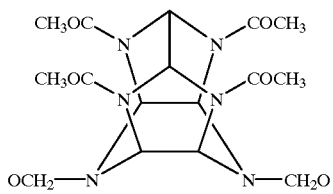

(IIIA)

The transformation from HBIW (I) to Compound IIIA is effected for example, with hydrogen in the presence of a palladium hydroxide-on-carbon catalyst and acetic anhydride using a bromobenzene catalyst. Subsequent conversion of Compound (IIIA) to CL-20 is effected using, in succession, the nitrating agents $NOBF_1$ and $NO_2BF_1$. These nitrating agents are very expensive. Also because of the fluorine present, waste products pose significant environmental problems. The expense of producing CL-20 by this synthesis is a significant limitation to its general usefulness in the propellant and explosive industries.

Accordingly, it is a general object of the invention of provide methods of syntheses of CL-20 and related energetic compounds, which methods are an improvement from the standpoint of cost and environmental impact.

It is a further object of the invention to provide novel chemical intermediates which can be converted to CL-20 and related high-energy caged nitrogen compounds.

SUMMARY OF THE INVENTION

In accordance with the invention, HBIW (Compound I) is chemically converted to an intermediate compound having the general formula:

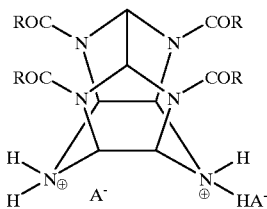

(IV)

where the R's are the same or different and are selected from the group consisting of alkyl, cycloalkyl, aryl, arylalkyl, alkene, alkyne, substituted forms of any of these groups, e.g. with halogens or nitro groups, or H; a group consisting of ($H^+A^-$) (a hydrogen ion and a complementary anion) is present on neither, one or both of the 4 and 10 nitrogens. Equivalently divalent anions may complement the $H^+$ ions on the two 4 and 10 nitrogens. Compounds of general formula (IV) may be produced, for example, by first converting HBIW to compound IIIA by the referenced method of A. T. Nielsen supra. and then converting compound IIIA to a compound of formula (IV) by catalytic transfer hydrogenolysis.

Compounds of formula (IV) may be nitrated to produce a compound of the formula:

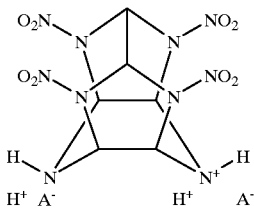

(V)

in which a group ($H^+A^-$) is present on neither, one or both of the 4 and 10 nitrogens. Compounds of formula (V) having two ($H^+A^-$) groups (the bis salt) and in which $A^-$ is an energetic anion, such as $CO_3^-$ or $ClO_4^-$ are useful high energy compounds.

Compounds of formula (IV) may also be reacted with an acylating agent, such as an acid anhydride or an acid chloride, to produce a hexaamide of the following formula:

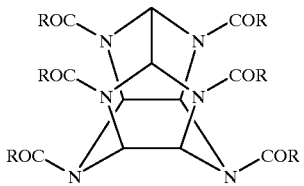

(VI)

where the R's are the same or different and are selected from the group consisting of alkyl, cycloalkyl, aryl, arylalkyl, alkene, alkyne, substituted forms of any of these groups, e.g. with halogens or nitro groups, or H.

Compounds of formula (VI) may be converted by nitrolysis nitration to CL-20 using a strong nitrating agent.

DETAILED DESCRIPTION OF CERTAIN PREFERRED EMBODIMENTS

Generally in accordance with the improved synthesis of CL-20, HBIW formula (I) is chemically transformed to a hexaamide of formula (VI). A hexaamide of formula (VI) can be reacted with a strong nitrating agent, such as $N_2O_5$ in nitric acid or a nitric acid/sulfuric acid mixture, to produce CL-20. These nitrating agents are much less expensive than $NOBF_4$ and $NO_2BF_4$, heretofore required in the above referenced method of A. T. Nielsen et al. for producing CL-20. HBIW is a known compound and its synthesis will not be described further herein. It is understood that equivalents of HBIW (I) might also be used, e.g., HBIW (I) with substitutions on one or more of the aromatic rings.

The presently preferred route for transforming HBIW to a compound of formula (VI) is to first convert HBIW to a compound of formula (III) by the above-referenced method of A. T. Nielsen et al.; formula (III) is as follows:

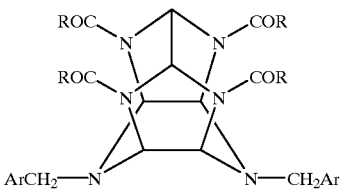

(III)

where the R's are the same or different and are selected from the group consisting of alkyl, cycloalkyl, aryl, arylalkyl, alkene, alkyne, substituted forms of any of these groups, or H. (Compound (IIIA) is the compound of Formula (III) wherein all four R's are $CH_3$ and Ar is phenyl). Ar is generally a phenyl group, although another aromatic group, substituted or unsubstituted, is considered to be equivalent.

Compounds of formula (III) are converted to compounds of general formula (IV) by hydrogenolysis. At the present time, a catalytic transfer hydrogenolysis is used. Catalytic transfer hydrogenolysis and reagents and catalysts therefore are described, for example, in (R. A. W. Johnstone et al. *Chem Rev.*, 85, 129–170 (1985)), the teachings of which are incorporated herein by reference. One useful method of effecting the catalytic transfer hydrogenolysis is using formic acid as the hydrogen donor in the presence of a palladium-on-carbon catalyst. The formic acid is generally used in a large molar excess, e.g., as the solvent for the reaction. Depending upon the reaction conditions used, a compound of formula (IV) is produced which is the bis salt (two ($H^+A^-$) groups ($A^-$ here being formate anion)), the mono formate salt or the free base. It is found that if formic acid is used neat with the Pd/C catalyst, the bis salt tends to be produced, a mixed water/formic acid solvent system tends to produce the mono salt; and a formic acid/methanol solvent system tends to produce the free base. Synthesis of the free base is often preferred to synthesis of either the bis or the mono salt; however, synthesis of the free base is less reproducible than synthesis of the bis or mono salt.

These reactions are exemplified as follows:

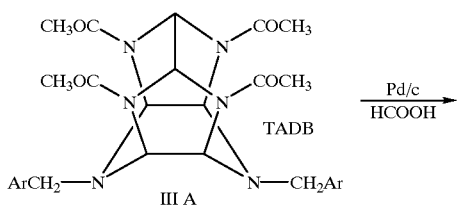

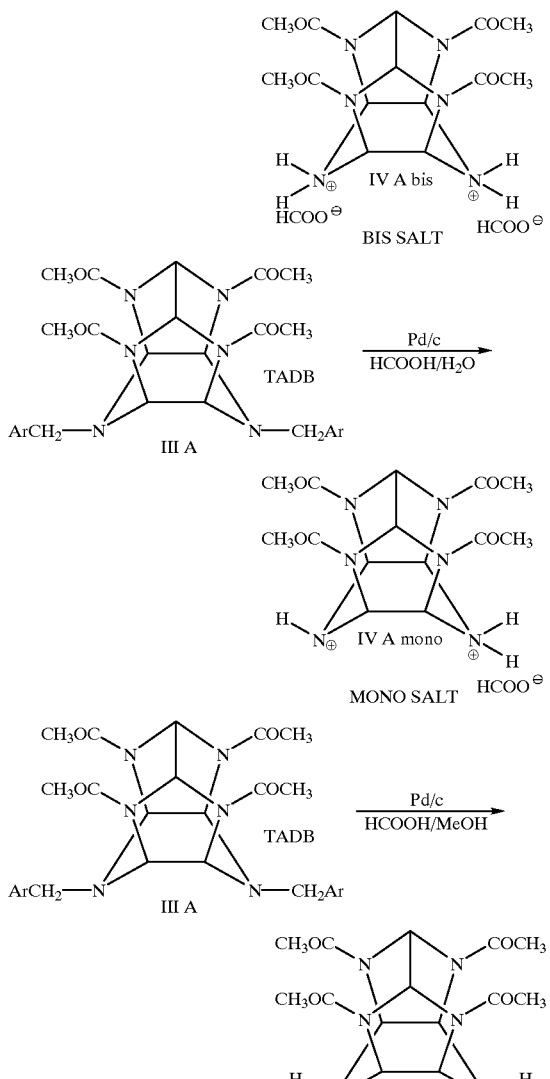

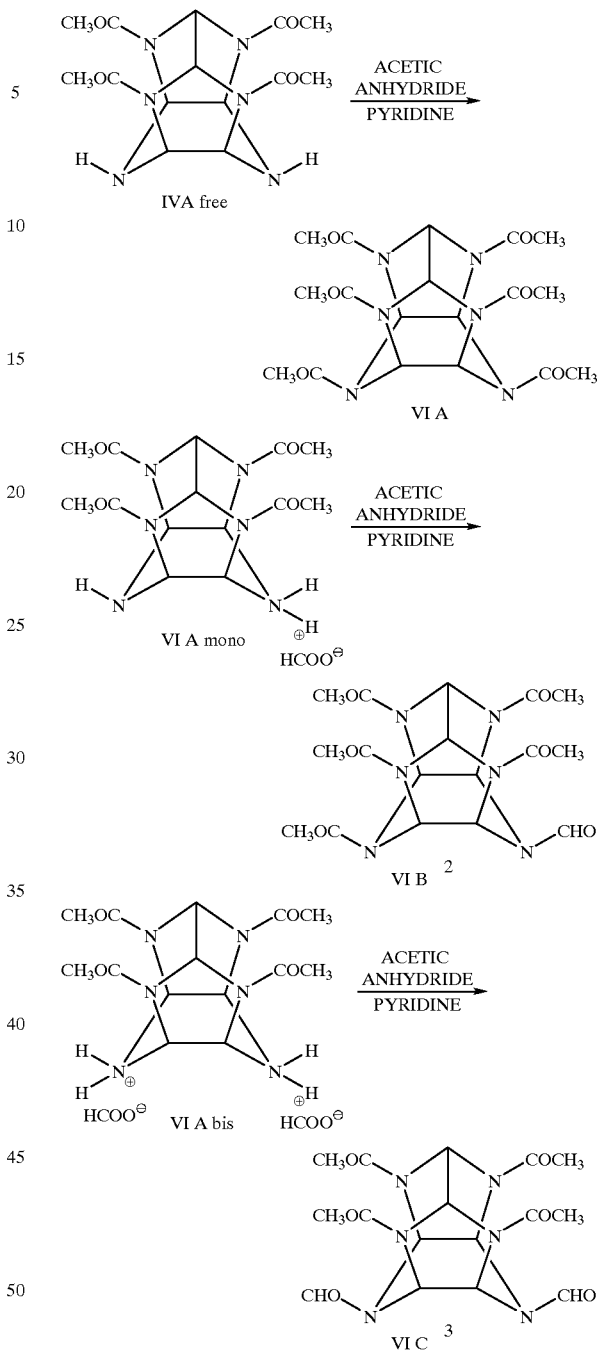

The novel compounds of formula (IV) are important intermediates for the production of CL-20 or for compounds of formula (V).

The bis or mono salts of formula (IV) may be converted to the free base by reaction with a strong base, such as an aqueous sodium hydroxide solution or a strongly basic anionic exchange resin, e.g., Dowex-50® in the OH form.

The 4 and 10 nitrogens of compounds of formula (IV) may be converted to hexaamide compounds of formula (VI) by reaction with an acylating agent, such as acid anhydride in the presence of a basic catalyst, such as pyridine. An acyl halide may alternatively be used as the acylating agent. If the free base is used, the reaction of the 4–10 nitrogens is a straight-forward acylation. If the bis or mono salt formate is acylated with acetic anhydride, the corresponding bis or mono N-formyl compound is obtained. Thus acylation using acetic anhydride of bis formate salt, mono formate salt and free base of formula (IV) compounds are compared in the following reactions:

Although the products of each reaction is slightly different, each of the products is of general formula (VI). Compounds of formula (VI) are likewise important intermediates in the synthesis of CL-20.

Compounds of Formula (VI) are converted to CL-20 with strong nitrating agents which produce nitramine groups at the 2, 4, 6, 8, 10 and 12 positions on the cage structure. Suitable agents include, but are not limited to $N_2O_5$ in nitric acid or a nitric acid/sulfuric acid mixture. This reaction is as follows:

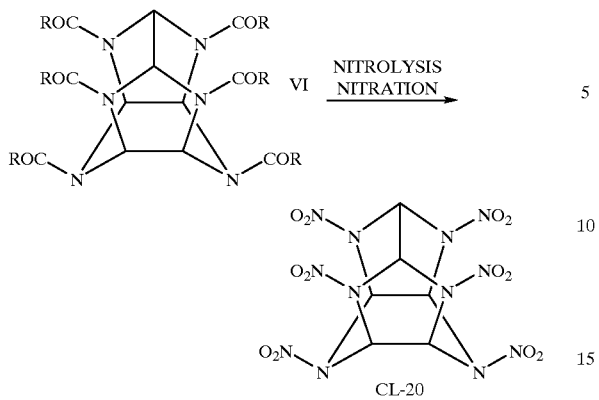

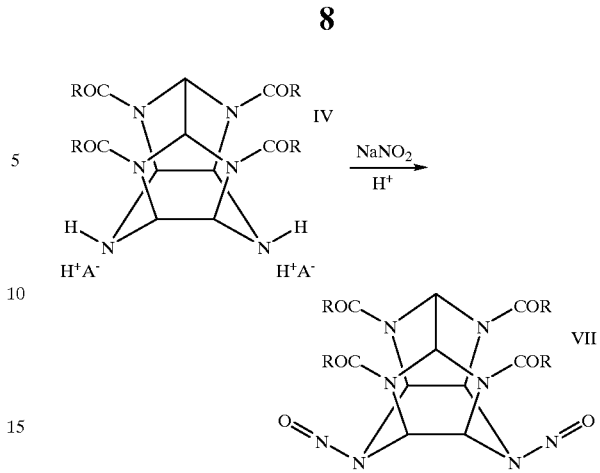

As mentioned above, Compounds of formula (IV) can also be converted to compounds of formula (V) by nitrolysis nitration by reaction with a strong nitrating agent, such as $N_2O_5$/nitric acid, or nitric acid/sulfuric acid, to produce a compound of formula (V). Subsequent reaction with an acid having an energetic anion, such as $NO_3^-$ or $ClO_4^-$, yields a highly energetic compound of formula V. These reactions are as follows:

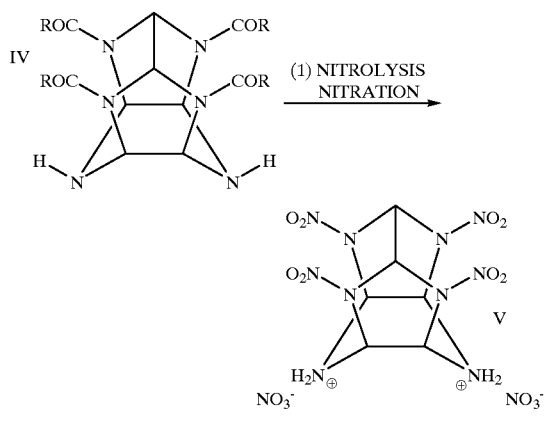

Nitrolysis nitration of a compound of formula IV may also produce some CL-20.

Compounds of formula V are most energetic in the form of bis salts of energetic anions, such as $NO_3^-$ or $ClO_4^-$. The nitration reaction produces the bis nitrate salt. To achieve a more energetic salt, the nitrate salt may be converted to a free base, e.g., by reaction with a base such as NaOH, and subsequently reacted with an acid having the energetic anion. Alternatively, the nitrate salt may be converted to a more energetic salt directly with an appropriate anion exchange resin.

As an alternative method of converting a compound of formula (IV) to CL-20, the compound is reacted with a nitrite, e.g., sodium nitrite in an aqueous acid, to produce a compound of the formula VII as shown in the following reaction.

This compound VII, when nitrated with a strong nitrating agent, such as $N_2O_5$ in nitric acid or a nitric acid/sulfuric acid mixture, undergoes a nitrolysis nitration reaction to produce CL-20 as follows:

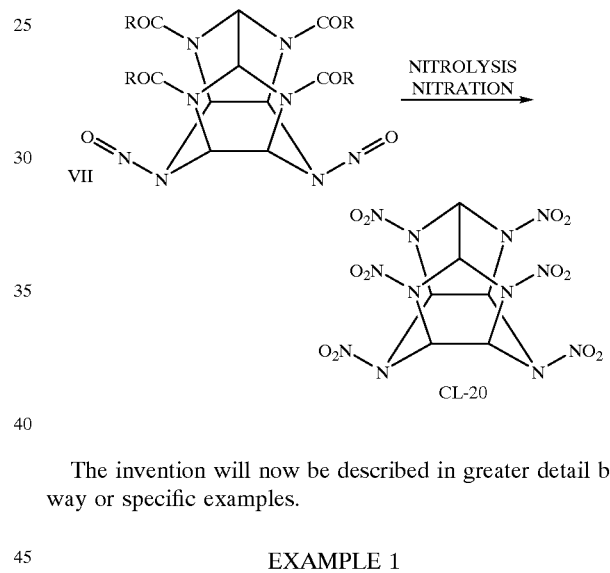

The invention will now be described in greater detail by way or specific examples.

EXAMPLE 1

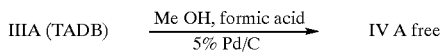

To a stirred slurry of 48.0 mg (0.093 mmole) of TADB in 4 ml of methanol and 0.2 ml of formic acid were added 51 mg of 5% Pd/C. The reaction was warmed to 40°–60° C. for 18 hours. The Pd/C and produce were removed by filtration. Extraction of the Pd/C with DMSO afforded the desired product.

$^1$H NMR (DMSO): 1.8.2.1 (multiplet, 12H, $CH_3CO$), 4.02–4.25 (multiplet, 2H, NH), 5.2–5.3 (multiplet, 4H, CH), 6.0–6.5 (multiplet, 2H, CH).

Upon heating to 150° C., the multiplet at 1.8.21, collapses to a singlet at 2.0, the multiplet at 4.02–4.25 collapses to a singlet at 3.7, the multiplet at 5.2–5.3 collapses to a singlet at 5.3 and the multiplet at 6.0–6.5 collapses to a singlet at 6.3.

EXAMPLE 2

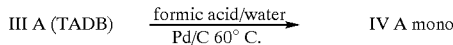

To a vigorously stirred solution of 10.0 g (19.36 mmole) of TADB in 200 ml of water were added 40 ml of formic acid; then 10.0 g of 5% Pd/C was added. The reaction was warmed to 60° C. After 18½ hr, the solids were filtered away from the solution and the volatiles were removed under reduced pressure to afford 7.9 g (106.7%) of mono formate salt.

$^1$H NMR (DMSO): 1.7–2.3 (multiplet, 12H, CH$_3$CO), 4.7–4.9 (broad double, 1H, NH, J=9.0 Hz), 5.5–5.7 (multiplet, 2H, CH), 6.0–6.8 (multiplet, 4H, CH), 8.3 (broad singlet, 4H, NH, HCO$_2$H).

Upon heating to 150° C., the multiplet at 1.7–2.3 collapses to 2 s, the bd at 4.7–4.9 moves to 4.3 and broadens, the multiplet at 5.5–5.7 collapses to a doublet at 5.6 (J=6 Hz), and the broad singlet at 8.3 splits into 2 singlets at 8.32 and 8.39.

EXAMPLE 3

To a stirred slurry of 10.0 g (19.36 mmol) of TADB in 200 ml of formic acid were added 10.0 g of 5% Pd/C. After 18 hours, the Pd/C was removed by filtration and the formic acid was removed under reduced pressure to afford 8.78 g (104%) of the desired bis salt.

$^1$H NMR (DMSO): 1.9–2.2 (multiplet, 12H, CH$_3$CO), 6.1–6.8 (multiplet, 6H, CH), 8.1–8..4 (multiplet, 6$^+$H, NH, HCO$_2$H).

Upon heating to 150° C., the multiplet at 1.9–2.2 collapses to a singlet and the other 2 multiplets begin to collapse.

EXAMPLE 4

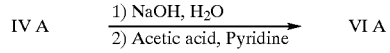

To 500 mg (1.17 mmol) of bis formate salt were added 2.4 ml of 1M NaOH). All volatiles were removed under reduced pressure. The residue was dissolved in 20 ml of acetic anhydride and 5 ml of pyridine and heated at 60° C. overnight. After 18 hours, the volatiles were removed and the residue treated with 10 ml of EtOAc. The solution was filtered and concentrated. The residue was passed through a plug of silica get using acetone as eluent giving VI A as an impure solid.

$^1$H NMR (CHCl$_3$): 2.05–2.2 (multiplet, 12H, CH$_3$CO), 2.45 (singlet, 6H, CH$_3$CO), 6.3–6.5 (multiplet, 4H, CH), 6.8–7.0 (multiplet, 2H, CH).

Upon heating to 150° C. (DMSO solvent), the multiplet at 2.05–2.2 collapses to a singlet. The multiplet at 6.3–6.5 and 6.8–7.0 each begin to collapse.

EXAMPLE 5

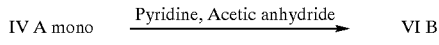

To a stirred slurry of 5.0 g (13.1 mmol) of mono formate salt in 200 ml of acetic anhydride were added 50 ml of pyridine. After 20 hours, all volatiles were removed under reduced pressure. Then the residue was treated with 100 ml of EtOAc. A precipitate formed which was removed by filtration. The solvent was removed and the residue passed through a plug of silica get using acetone as eluent.

$^1$H NMR (CHCl$_3$): 2.06, 2.09, 2.12, 2.14 (4 singlet, 12H, CH$_3$CO), 2.42 (singlet, 3H, CH$_3$CO), 6.0–7.0 (multiplet, 6H, CH), 8.3 (singlet, 1H, CHO).

EXAMPLE 6

To a stirred slurry of 5.0 g (11.67 mmol) of bis formate salt (IV A bis) in 200 ml of acetic anhydride were added 50 ml of pyridine. After 20 hours, all volatiles were removed under reduced pressure. Then the residue was treated with 100 ml of EtOAc. A precipitate formed which was removed by filtration. The solvent was removed and the residue passed through a plug of silica gel using acetone as eluent. Obtained was 4.5 g (98.3%) yield of bis formyl compound. R$_f$=0.35 (acetone).

$^1$H NMR (CHCl$_3$): 2.0–2.3 (multiplet, 12H, CH$_3$CO), 6.06 (doublet, 0.2H, CH, J=4.8 Hz), 6.15 (broad singlet, 0.45H, CH), 6.26 (doublet, 1.5H, CH, J=7.8, 1.8 Hz), 6.46 (singlet, 1.7H, CH), 6.67 (doublet, 1.5H, CH, J=7.8, 1.81 Hz), 6.75–6.81 (multiplet, 0.65H, CH).

EXAMPLE 7

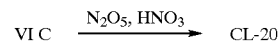

To 10 mg (0.026 mmol) of diformyl tetraacetyl compound VI C were added 2 ml of 5% N$_2$O$_3$ in nitric acid at 0° C. for 4.5 hours; the mixture was then diluted with water. The aqueous solution was extracted 4× with ethyl acetate. The organics were dried (MgSO$_4$) and concentrated to dryness. By thin layer chromatography (silica gel, multiple solvent systems). The produce exhibited an R$_f$ identical to CL-20 and a superimpossable $^1$H NMR spectrum.

EXAMPLE 8

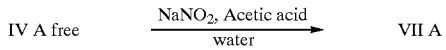

To 1.0 g of tetraacetyl (IV A free) in 2 ml of water and 2 ml of acetic acid were added 0.70 g of NaNo$_2$ in 2 ml of water at 0° C. Stirred 18 hours at room temperature. The desired produce precipitated from the reaction mixture and was collected by filtration in a quantitative yield.

While the invention has been described in terms of certain preferred embodiments, modifications obvious to one with ordinary skill in the art may be made without departing from the scope of the present invention.

Various features of the invention are set forth in the following claims.

What is claimed is:

1. A method of preparing an energetic compound having the formula II:

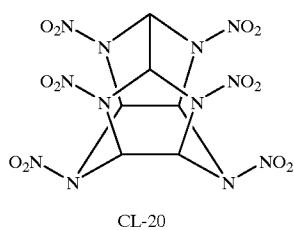

CL-20 comprising nitrating a compound having the formula VI:

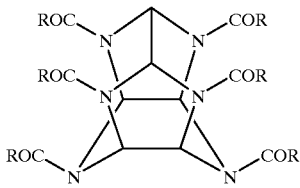

wherein R is selected from the group consisting of alkyl, cycloalkyl, aryl, arylalkyl, alkene, alkyne, substituted forms of any of these groups and H, with a strong nitrating agent.

2. A method according to claim 1, wherein said strong nitrating agent is $HNO_3$ or a $HNO_3/H_2SO_4$ mixture.

3. A method according to claim 1 wherein the compound having formula VI is obtained by acylating a compound having the formula IV:

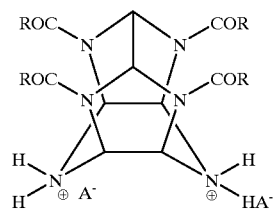

wherein said formula IV a group consisting of hydrogen ion and a complementary anion is present on neither, one or both of the nitrogens in the 4 and 10 positions, in the presence of at least one acylating agent.

4. A method according to claim 3, wherein said acylating gent is an acid chloride or carboxylic acid anhydride.

5. A method according to claim 3, wherein the compound having the formula IV is obtained by catalytic transformation hydrogenolysis of a compound having the formula (III):

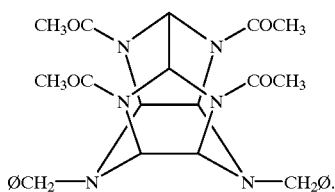

6. A method according to claim 5, wherein said hydrogenolysis is conducted in the presence of a palladium-on-carbon catalyst.

7. A method according to claim 3, wherein said compound represented by the formula IV is:

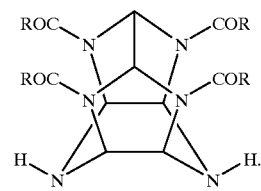

8. A method according to claim 3, wherein said compound represented by the formula (IV) has a group consisting of a hydrogen ion and a complementary anion associated with the nitrogen at the 4 or 10 positions.

9. A method according to claim 8, wherein said anion is an energetic anion.

10. A method according to claim 3, wherein said compound represented by the formula (IV) has a group consisting of a hydrogen ion and a complementary anion are associated with the nitrogen in each of the 4 and 10 positions.

11. A method according to claim 10, wherein each said anion is an energetic anion.

12. A method of preparing a compound having the formula IV:

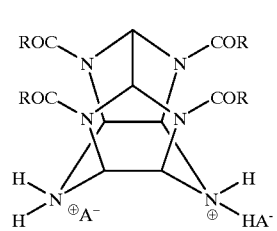

wherein said formula IV each R is independently selected from the group consisting of alkyl, cycloalkyl, aryl, arylalkyl, alkene, alkyne, a substituted form of any of these groups and H, and a group consisting of a hydrogen ion and a complementary anion is present on neither, one or both of the nitrogens in the 4 and 10 positions in said formula IV, the method comprising:

hydrogenolyzing a compound having the formula (III)

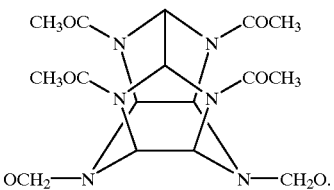
(III)

13. A method according to claim 12, wherein said compound is represented by the formula (IV) is:

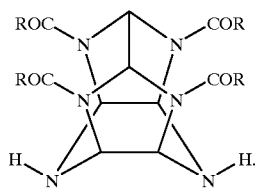

14. A method according to claim 12, wherein said compound represented by formula (IV) has a hydrogen ion and a complementary anion associated with the nitrogen at the 4 or 10 positions, each said complementary anion being an energetic anion.

15. A method according to claim 12, wherein said compound represented by formula (IV) has a hydrogen ion and a complementary anion associated with the nitrogen at the 4 and 10 positions, each said complementary anion being an energetic anion.

16. A method of preparing an energetic compound having the formula II:

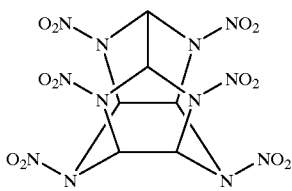
(II)

comprising:
nitrating a compound having the formula IV:

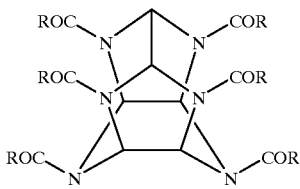
VI wherein R is selected from the group consisting of alkyl, cycloalkyl, aryl, arylalkyl, alkene, alkyne, substituted forms of any of these groups and H, with a strong nitrating agent selected from the group consisting of $HNO_3$ and $HNO_3/H_2SO_4$ mixture, wherein the compound having formula VI is obtained by conducting the catalytic transformation hydrogenolysis of a compound having the formula (III):

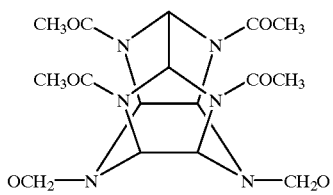
(III)

in the presence of a palladium-on-carbon catalyst to obtain a compound having the formula IV:

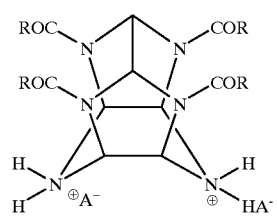
(IV)

wherein formula IV a group consisting of hydrogen ion and a complementary anion is present on neither, one or both of the nitrogens in the 4 and 10 positions; and acylating the compound having the formula IV in the presence of at least one acylating agent selected from the group consisting of an acid chloride and carboxylic acid anhydride to obtain the compound having the formula VI.

17. A method according to claim 16, wherein said compound is represented by the formula (IV) is:

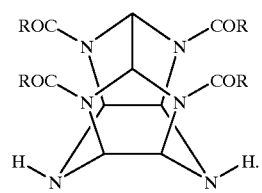

18. A method according to claim 16, wherein said compound represented by formula (IV) has a hydrogen ion and a complementary anion associated with the nitrogen at the 4 or 10 positions, each said complementary anion being an energetic anion.

19. A method according to claim 16, wherein said compound represented by formula IV has a hydrogen ion and a complementary anion associated with the nitrogen at the 4 and 10 positions, each said complementary anion being an energetic anion.

* * * * *

UNITED STATES PATENT AND TRADEMARK OFFICE
CERTIFICATE OF CORRECTION

PATENT NO.       : 6,147,209
APPLICATION NO.  : 07/989369
DATED            : November 14, 2000
INVENTOR(S)      : Wardle et al.

Page 1 of 5

It is certified that error appears in the above-identified patent and that said Letters Patent is hereby corrected as shown below:

On the title page:
In the section (56) References Cited,
OTHER PUBLICATIONS:   change "12-Hexaazaisowurtzita," to --12-Hexaazaisowurtzitane,--

| | | |
|---|---|---|
| COLUMN 1, | LINE 7, | change "division of application" to --division of pending application-- |
| COLUMN 1, | LINE 15, | change "Arnold T. Nielsen in a paper entitled" to --Arnold T. Nielsen, in a paper titled-- |
| COLUMN 1, | LINE 21, | change "$_9$]dodecane." to --$^9$]dodecane.-- and change "entitles" to --titled-- |
| COLUMN 1, | LINE 23, | change " "synthesis of a caged nitramine" " to --"Synthesis of a Caged Nitramine"-- |
| COLUMN 1, | LINE 27, | change "12-hexaayatetracyclo [5.5.0.0.$^{3,11}$0.$^{5,9}$]dodecane" to --12-hexaazatetracyclo[5.5.0.0.$^{3,11}$0.$^{5,9}$]dodecane-- |
| COLUMN 1, | LINE 28, | change "(This" to --(this-- |
| COLUMN 1, | LINES 46-58, | in chemical structure diagram (I): change all occurrences of "OCH$_2$" to --ØCH$_2$-- change all occurrences of "CH$_2$O" to --CH$_2$Ø-- change "4" to --11-- (appearing at line 56 right of center) change "N$_{11}$" to --N$_4$--(appearing at line 57 left of center) |
| COLUMN 2, | LINES 22-35, | in chemical structure diagram (IIIA): change "OCH$_2$" to --ØCH$_2$-- change "CH$_2$O" to --CH$_2$Ø-- |
| COLUMN 2, | LINE 42, | change "Also" to --Also,-- |
| COLUMN 2, | LINE 49, | change "invention of" to --invention to-- |
| COLUMN 2, | LINE 57, | insert a comma --,-- after "chemical intermediates" |
| COLUMN 3, | LINE 13, | change "where the R's are" to --where each "R" is-- and change the second occurrence of "are" to --is-- |

UNITED STATES PATENT AND TRADEMARK OFFICE
CERTIFICATE OF CORRECTION

PATENT NO. : 6,147,209
APPLICATION NO. : 07/989369
DATED : November 14, 2000
INVENTOR(S) : Wardle et al.

It is certified that error appears in the above-identified patent and that said Letters Patent is hereby corrected as shown below:

| | | |
|---|---|---|
| COLUMN 3, | LINES 27-38, | in chemical structure diagram (V): change "N$^+$" to --N-- (appearing at line 36 on right side) |
| COLUMN 3, | LINE 42, | after "ClO$_4$$^-$" insert a comma --,-- |
| COLUMN 3, | LINE 57, | change "where the R's are" to --where each "R" is-- and change the second occurrence of "are" to --is-- |
| COLUMN 3, | LINE 60, | change "or H." to --and H.-- |
| COLUMN 4, | LINE 28, | change "where the R's are" to --where each "R" is-- and change the second occurrence of "are" to --is-- |
| COLUMN 4, | LINE 30, | change "groups, or" to --groups, and-- |
| COLUMN 4, | LINE 32, | change "R's" to --"R's"-- |
| COLUMN 4, | LINE 47, | after "is produced" insert a comma --,-- |
| COLUMN 4, | LINE 51, | change "be produced," to --be produced;-- |
| COLUMN 4, | LINES 58-67, | in chemical structure diagram IIIA: change "Pd/c" to --Pd/C-- (appearing at line 62 at right) |
| COLUMN 5, | LINES 11-19, | in chemical structure diagram IIIA: change "Pd/c" to --Pd/C-- (appearing at line 14 at right) |
| COLUMN 5, | LINES 20-28, | in chemical structure diagram IV A mono: change "N$_\oplus$" to --N-- (appearing at line 26 at left) |
| COLUMN 5, | LINES 29-36, | in chemical structure diagram IIIA: change "Pd/c" to --Pd/C-- (appearing at line 14 at right) |
| COLUMN 6, | LINE 9, | change "IVA free" to --IV A free-- |
| COLUMN 6, | LINES 18-27, | in chemical structure diagram VI A mono: change "N" to --$_\oplus$N-- (appearing at line 24 at right) change "$_\oplus$H" to --H-- (appearing at line 25 at right) |

UNITED STATES PATENT AND TRADEMARK OFFICE
CERTIFICATE OF CORRECTION

PATENT NO. : 6,147,209
APPLICATION NO. : 07/989369
DATED : November 14, 2000
INVENTOR(S) : Wardle et al.

Page 3 of 5

It is certified that error appears in the above-identified patent and that said Letters Patent is hereby corrected as shown below:

| | | |
|---|---|---|
| COLUMN 6, | LINES 36-44, | in chemical structure diagram VI A bis: change "N" to --⊕N-- (appearing at line 42 at right) change "⊕H" to --H-- (appearing at line 43 at right) |
| COLUMN 6, | LINE 56, | change "reaction is" to --reaction are-- |
| COLUMN 6, | LINE 62, | change "Formula" to --formula-- |
| COLUMN 6, | LINE 63, | change "agents which" to --agents, which-- |
| COLUMN 6, | LINE 65, | change "limited to" to --limited to,-- |
| COLUMN 8, | LINE 43, | change "way or specific to" to --way of specific-- |
| COLUMN 8, | LINE 52, | change "mmole)" to --mmol)-- |
| COLUMN 8, | LINE 59, | change "1.8.2.1" to --1.8–2.1-- |
| COLUMN 8, | LINE 63, | change "1.8.21," to --1.8–2.1,-- |
| COLUMN 9, | LINE 7, | change "mmole)" to --mmol)-- |
| COLUMN 9, | LINE 10, | change "18½ hr," to --18.5 hours,-- |
| COLUMN 9, | LINE 38, | change "8.1–8..4" to --8.1–8.4-- and change "$6^+H$," to --6H,-- |
| COLUMN 9, | LINE 59, | change "silica get" to --silica gel-- and "as eluent" to --as the eluent-- |
| COLUMN 10, | LINE 10, | after "Then" insert a comma --,-- |
| COLUMN 10, | LINE 11, | after "formed" insert a comma --,-- |
| COLUMN 10, | LINE 13, | change "silica get" to --silica gel-- and "as eluent." to --as the eluent.-- |
| COLUMN 10, | LINE 26, | after "Then" insert a comma --,-- |
| COLUMN 10, | LINE 27, | after "formed" insert a comma --,-- |
| COLUMN 10, | LINE 29, | change "as eluent." to --as the eluent.-- |
| COLUMN 10, | LINE 45, | change "VI C" to --(VI C)-- |
| COLUMN 10, | LINE 50, | change "systems). The produce" to --systems), the product--. |
| COLUMN 10, | LINE 51, | change "superimpossable" to --superimposable-- |
| COLUMN 10, | LINE 61, | change "Stirred 18 hours" to --The reaction mixture was stirred for 18 hours-- |
| COLUMN 10, | LINE 62, | change "desired produce precipitated" to --desired product precipitated-- |

UNITED STATES PATENT AND TRADEMARK OFFICE
CERTIFICATE OF CORRECTION

PATENT NO.      : 6,147,209
APPLICATION NO. : 07/989369
DATED           : November 14, 2000
INVENTOR(S)     : Wardle et al.

It is certified that error appears in the above-identified patent and that said Letters Patent is hereby corrected as shown below:

In the claims:

| | | | |
|---|---|---|---|
| CLAIM 1, | COLUMN 11, | LINE 23, | in chemical formula VI: change the lowermost occurrence of "VI" to --(VI)-- |
| CLAIM 12, | COLUMN 12, | LINE 56, | change "N" to --$_\oplus$N-- (appearing at the left) |
| CLAIM 12, | COLUMN 12, | LINE 57, | change "$_\oplus$A$^-$" to --A$^-$-- (appearing at the left) |
| CLAIM 12, | COLUMN 13, | LINES 2-10, | in chemical formula diagram (III): change "OCH$_2$" to --ØCH$_2$-- (appearing at line 10 at left) change "CH$_2$O." to --CH$_2$Ø.-- (appearing at line 10 at right) |
| CLAIM 16, | COLUMN 13, | LINE 35, | change "II:" to --(II):-- |
| CLAIM 16, | COLUMN 13, | LINE 48, | change "the formula IV:" to --the formula VI:-- |
| CLAIM 16, | COLUMN 13, | LINE 50, | change "VI" to --(VI)-- |
| CLAIM 16, | COLUMN 14, | LINES 6-15, | in chemical formula diagram (III): change "OCH$_2$" to --ØCH$_2$-- (appearing at line 14 at right) change "CH$_2$O" to --CH$_2$O-- (appearing at line 14 at left) |
| CLAIM 16, | COLUMN 14, | LINES 20-30, | in chemical formula diagram (IV): |
| CLAIM 16, | COLUMN 14, | LINE 27, | change "N" to --$_\oplus$N-- (appearing at the left) |

UNITED STATES PATENT AND TRADEMARK OFFICE
CERTIFICATE OF CORRECTION

PATENT NO. : 6,147,209
APPLICATION NO. : 07/989369
DATED : November 14, 2000
INVENTOR(S) : Wardle et al.

It is certified that error appears in the above-identified patent and that said Letters Patent is hereby corrected as shown below:

In the claims (continued):

CLAIM 16, COLUMN 14, LINE 28, change "$_\oplus A^-$" to --$A^-$-- (appearing at the left)

Signed and Sealed this

Nineteenth Day of September, 2006

JON W. DUDAS
*Director of the United States Patent and Trademark Office*